United States Patent [19]
Mayes

[11] Patent Number: 6,100,526
[45] Date of Patent: *Aug. 8, 2000

[54] GRAIN QUALITY MONITOR

[75] Inventor: David M. Mayes, LaGrande, Oreg.

[73] Assignee: DSquared Development, Inc., La Grande, Oreg.

[*] Notice: This patent issued on a continued prosecution application filed under 37 CFR 1.53(d), and is subject to the twenty year patent term provisions of 35 U.S.C. 154(a)(2).

[21] Appl. No.: 09/019,667

[22] Filed: Feb. 6, 1998

Related U.S. Application Data

[63] Continuation-in-part of application No. 08/777,228, Dec. 30, 1996, abandoned.

[51] Int. Cl.$^7$ .................................................. G01N 21/35
[52] U.S. Cl. .............................. 250/339.11; 250/339.11
[58] Field of Search ................................. 356/419, 328, 356/346, 237; 250/339.11, 339.02, 910

[56] References Cited

U.S. PATENT DOCUMENTS

| | | | |
|---|---|---|---|
| 4,260,262 | 4/1981 | Webster | 356/418 |
| 4,266,878 | 5/1981 | Auer | 356/419 |
| 4,286,327 | 8/1981 | Rosenthal et al. | 364/498 |
| 4,540,286 | 9/1985 | Satake et al. | 356/445 |
| 4,627,008 | 12/1986 | Rosenthal | 364/550 |
| 4,692,620 | 9/1987 | Rosenthal | 250/343 |
| 4,752,689 | 6/1988 | Satake | 250/339 |
| 4,806,764 | 2/1989 | Satake | 250/339 |
| 4,997,280 | 3/1991 | Norris | 356/308 |
| 5,021,662 | 6/1991 | Johnson | 250/339 |
| 5,092,819 | 3/1992 | Schroeder et al. | 460/7 |
| 5,106,339 | 4/1992 | Braun et al. | 460/7 |
| 5,159,199 | 10/1992 | LaBaw | 356/328 |
| 5,166,755 | 11/1992 | Gat | 356/419 |
| 5,206,699 | 4/1993 | Stewart et al. | 356/30 |
| 5,218,207 | 6/1993 | Rosenthal | 250/341 |
| 5,241,178 | 8/1993 | Shields | 250/339 |
| 5,258,825 | 11/1993 | Reed et al. | 356/419 |

(List continued on next page.)

FOREIGN PATENT DOCUMENTS

| | | |
|---|---|---|
| 0 806 653 A1 | 5/1997 | European Pat. Off. . |
| 2938-844 | 9/1979 | Germany . |

OTHER PUBLICATIONS

Wetzel, D., "Near–Infrared Reflectance Analysis, Sleeper Among Spectroscopic Techniques," *Analytical Chemistry*, 55(12):1165A–1176A (Oct. 1983).

Goddu, R.F., and Delker, D.A., "Spectra–Structure Correlations for the Near–Infrared Region," Aids for the Analyst. In *Analytical Chemistry*, 32(1):140–141 (Jan. 1960).

Mosen, A.W., and Buzzelli, G., "Determination of Impurities in Helim by Gas Chromatography," Aids for the Analyst. In *Analytical Chemistry*, 32(1):141–142 (Jan. 1960).

Starr, C., et al., "Applications of Near Infrared Reflectance Analysis in Breeding Wheats for Bread–making Quality," Near Infrared Analysis—Today or Tomorrow?" In *Anal. Proc.*, 20:72–74 (Feb. 1983).

(List continued on next page.)

*Primary Examiner*—Frank G. Font
*Assistant Examiner*—Tu T. Nguyen
*Attorney, Agent, or Firm*—Hamilton, Brook, Smith & Reynolds, P.C.

[57] ABSTRACT

Percentage concentrations of constituents of a sample of cereal grain or other agricultural product in a flowing stream are determined while harvesting or processing using a short wave near infrared analyzer. The analyzer irradiates the sample, picks up diffuse reflectance of individual wavelengths from the sample and spatially separates the diffuse reflectance into a response at individual wavelengths. The result is to simultaneously detect the intensities of the individual wavelengths in parallel from the same portion of the product being analyzed. Percentage constituents of the composite substance may then be compared with known percentage constituents to determine the constituents. The analyzer is optically stabilized and is therefore suitable for attaching to the agricultural combine to perform real time measurements in the field.

47 Claims, 4 Drawing Sheets

U.S. PATENT DOCUMENTS

| | | | |
|---|---|---|---|
| 5,319,200 | 6/1994 | Rosenthal et al. | 250/341 |
| 5,327,708 | 7/1994 | Gerrish | 56/1 |
| 5,351,117 | 9/1994 | Stewart et al. | 356/30 |
| 5,406,084 | 4/1995 | Tobler et al. | 250/339.01 |
| 5,460,177 | 10/1995 | Purdy et al. | 128/633 |
| 5,476,108 | 12/1995 | Dominguez et al. | 131/108 |
| 5,480,354 | 1/1996 | Sadjadi | 460/7 |
| 5,616,851 | 4/1997 | McMahon et al. | 73/29.01 |
| 5,642,498 | 6/1997 | Kutner | 395/157 |
| 5,736,410 | 4/1998 | Zarling et al. | 356/346 |
| 5,751,421 | 5/1998 | Wright et al. | 356/328 |

OTHER PUBLICATIONS

Winch, J.E., and Major, H., "Predicting Nitrogen and Digestibility of Forages Using Near Infrared Reflectance Photometry," *Canadian Journal of Plant Science* 61:45–51 (Jan. 1981).

"Discriminant Analysis of Black Tea by Near Infrared Reflectance Spectroscopy," In *Food Chemistry*, G.G. Birch et al., eds. (England: Elsevier Applied Science Publishers Ltd.) 29(1):233–238 (1988).

Kisner, H.J, et al., "Multiple Analytical Frequencies and Standards for the Least–Squares Spectrometric Analysis of Serum Lipids," *Analytical Chemistry*, 55(11):1703–1707 (Sep. 1983).

Ciurczak, E.W., "Uses of Near–Infrared Spectroscopy in Pharmaceutical Analysis," *Applied Spectroscopy Reviews*, 23(1&2):147–163 (1987).

Geladi, P., et al., "Linearization and Scatter–Correction for Near–Infrared Reflectance Spectra of Meat," *Applied Spectroscopy*, 39(3):491–500 (1985).

Nyden, M.R., et al., "Spectroscopic Quantitative Analysis of Strongly Interacting Systems: Human Plasma protein Mixtures," *Applied Spectroscopy* 42(4):588–594 (1988).

Watson, C.A., "Near Infrared Reflectance Spectrophotometric Analysis of Agricultural Products," Instrumentation, In *Analytical Chemistry*, 49(9);835A–840A (Aug. 1977).

Josefson, Mats, et al., "Optical Fiber Spectrometry in Turbid Solutions by Multivariate Calibration Applied to Tablet Dissolution Testing," *Analytical Chemistry*, 60(24):2666–2671 (Dec. 15, 1988).

Honigs, D.E., et al., "Near–Infrared Reflectance Analysis by Gauss–Jordan Linear Algebra," *Applied Spectroscopy*, 37(6):Errata, 491–497 (1983).

Honigs, D.E., et al., "A New Method for Obtaining Individual Component Spectra from Those of Complex Mixtures," *Applied Spectroscopy*, 38(3):317–322 (1984).

Stark, E., and Luchter, K., "Near–Infrared Analysis (NIRA): A Technology for Quantitative and Qualitative Analysis," *Applied Spectroscopy Reviews*, 22(4):335–399 (1986).

Norris, K.H., et al., "Predicting Forage Quality by Infrared Reflectance Spectroscopy," *Journal of Animal Science*, 43(4):889–897 (1976).

Keefe, P.D., "A dedicated wheat grain image analyser," *Plant Varieties and Seeds*, 5:27–33 (1992).

Suppliers of Kestrel™ brand systems for imaging spectroscopy. Rhea Corporation Home Page, http://home.navisoft.com/rheacorp/ (Sep. 22, 1997 6:57 AM).

Yamamoto, K.Y., et al., "Detection of Metals in the Environment Using a Portable Laser–Induced Breakdown Spectroscopy Instrument," Detection of Metals in the Environment Us . . . Induced Breakdown Spectroscopy Instrument, http://esther.la.asu.edu/sas/journal/ASv50n2/ ASv50n2_sp12.html (Sep. 22, 1997 7:08 AM).

Baird, W., and Nogar, N.S., "Compact, Self–Contained Optical Spectrometer," Compact, Self–Contained Optical Spectrometer, http://esther.la.asu.edu/sas/journal/ASv49n11/ Asv49n11–sp20.html (Sep. 22, 1997 7:12 AM).

"Perstorp Analytical," Perstorp Analytical Products, http://www.i–way.net.uk/sinar/products/ (Sep. 22, 1997 7:31 AM).

"Grain Flow and Moisture Sensor Calibration," Department of Biosystems and Agricultural Engineering, http://www.bae/umn/edu/annrpt/1995/research/mach1.html (Sep. 22, 1997 7:33 AM).

Lutton, C., "Cyberfarm," Computers/Communications, In *Forbes*, pp. 86–87 (Jul. 15, 1996).

"Infrared detectors," Near Infrared Spectroscopy in Food Analysis, In *Fundamentals of Near Infrared Instrumentation*, pp. 71–73 (undated).

"Better Crops With Plant Food," 81(4) (1997).

Schneider, I., et al., "Fiber–Optic Near–Infrared Reflectance Sensor for Detection of Organics in Soils," *IEEE Photonics Technology Letters*, 7(1):87–89 (Jan. 1995).

Baughman, E., et al., "NIR applications in process analysis," *American Laboratory*, pp. 54–58 (Oct. 1989).

Mayes, D., et al., "A compact, solid state spectrophotometer system for process monitoring," *Process Control and Quality*, 5:1–8 (1993).

Dsquared Development, Inc., "Complex Problems??—Simple Answers!!,", product brochure, date unknown.

GRAIN QUALITY MONITOR

RELATED APPLICATION

This is a Continuation-in-part of prior application Ser. No. 08/777,228, filed Dec. 30, 1996, now abandoned.

BACKGROUND OF THE INVENTION

It has been long recognized that the value of agricultural products such as cereal grains and the like are affected by the quality of their inherent constituent components. In particular, cereal grains with desirable protein, oil, starch, fiber, and moisture content and desirable levels of carbohydrates and other constituents can command a premium price. Favorable markets for these grains and their processed commodities have therefore created the need for knowing content and also various other various physical characteristics such as hardness.

To meet market expectations, numerous analyzer systems have been developed using near infrared (NIR) spectroscopy techniques to analyze the percentage concentrations of protein and moisture. Some of these systems target cereal grains in milled form as explained, for example, in U.S. Pat. No. 5,258,825. The value added by milling in some instances decreases the economic gain that is obtained by first sorting, and thus others target the analysis of whole grains, as in U.S. Pat. No. 4,260,262.

NIR spectrophotometric techniques are typically favored because of their speed, requiring typically only thirty to sixty seconds to provide results, as compared with the hours of time which would be needed to separate and analyze constituents using wet chemical and other laboratory methods. NIR spectrophotometric techniques are also favored because they do not destroy the samples analyzed. In a typical analysis of wheat grains, for example, a sample is irradiated serially with selected wavelengths. Next, either the sample's diffuse transmissivity or its diffuse reflectance is measured. Either measurement then lends itself to use in algorithms that are employed to determine the percentage concentration of constituents of a substance.

For example, the analyzer described in U.S. Pat. No. 4,260,262 determines the percentage of oil, water, and protein constituents by using the following equations:

oil $\% = K_0 + K_1 (\Delta OD)_w + K_2 (\Delta OD)_o + K_3 (\Delta OD)_p$ water $\% = K_4 + K_5 (\Delta OD)_w + K_6 (\Delta OD)_o + K_7 (\Delta OD)_p$ protein $\% = K_8 + K_9 (\Delta OD)_w + K_{10} (\Delta OD)_o + K_{11} (\Delta OD)_p$ where $(\Delta OD)_w$ represents the change in optical density using a pair of wavelengths sensitive to the percentage moisture content, $(\Delta OD)_o$ represents the change in optical density using a pair of wavelengths sensitive to the percentage oil content, and $(\Delta OD)_p$ represents the change in optical density using a pair of wavelengths sensitive to the percentage protein consents. $K_0$–$K_1$ are constants or influence factors.

The change in optical density of any given constituent may thus be found from the following equation:

$\Delta OD = \log (Ii/Ir)_1 - \log (Ii/Ir)_2$ where $(Ii/Ir)_1$ is the ratio of the intensity of incident light to the intensity of reflected light at one selected wavelength, and $(Ii/Ir)_2$ is the ratio of the intensity of incident light to the intensity of reflected light at a second selected wavelength. Typically, grain analyzers use selected wavelengths in the range of about 1100 to 2500 nanometers. However, in U.S. Pat. No. 5,258,825, particle size effects of flour were overcome by additionally using a 540 nanometer wavelength.

Analyzers of the prior art typically use a filter wheel or scanning diffraction grating to serially generate the specific wavelengths that are of interest in analyzing grain constituents. Because of moving parts, filter wheels and scanning diffraction gratings are sensitive to vibration and are not reliable in analyzing grain during harvesting. They therefore are not suitable for withstanding the mechanical vibrations generated by a combine or other agricultural harvesting equipment, and therefore have not found use in real-time measurement of grain constituents during harvesting.

SUMMARY OF THE INVENTION

This invention is concerned with a near infrared (NIR) analysis system and method for determining percentage concentration of constituents in a flowing stream of agricultural products and related substances as they are fed through a combine harvester, grain processing, or storage equipment. Such agricultural products may include, but are not limited to, for example, cereal grains such as wheat, corn, rye, oats, barley, rice, soybeans, amaranth, triticale, and other grains, grasses and forage materials.

The invention uses the diffuse reflectance properties of light to obtain percentage concentrations of constituents of the flowing stream of an agricultural substance. The techniques involved measure a spectral response to short wavelength, near infrared (NIR) radiant energy in the range from 600 to about 1100 nanometers (nm) as well as light in the visible spectrum, including wavelengths as low as about 570 nanometers (nm). The spectral response at shorter wavelengths helps in the modeling of proteins and other constituents in conjunction with the response at higher wavelengths.

The analysis system includes an optical head having a suitably broad bandwidth light source for irradiating the flowing agricultural product stream simultaneously with multiple radiation wavelengths. A light pickup receives radiation diffusely reflected from a discrete portion of the flowing substance being analyzed. The pickup in turn passes the received light along a fiber optic cable to a detection and computation subsystem which may be mounted at some distance away from the optical head.

Within the subsystem, a mode mixer first receives the light. The mode mixer in turn passes the received light through a mechanically stable fiber to an optical detection block. The optical detection block consists of a fiber coupling and a pair of cylindrical lenses. The cylindrical lenses in turn pass light to a wavelength separator, such as a linear variable filter (LVF), to spatially separate the wavelengths of interest.

The spatial separator in turn feeds a suitable response detector, such as a charge coupled device (CCD), which is capable of individually detecting in parallel, and at the same time, multiple wavelengths of the diffusely reflected radiation. The responses at individual wavelengths are then detected and converted to suitable form such as digital data, to then calculate the percentage concentration of the various constituents of the substance.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
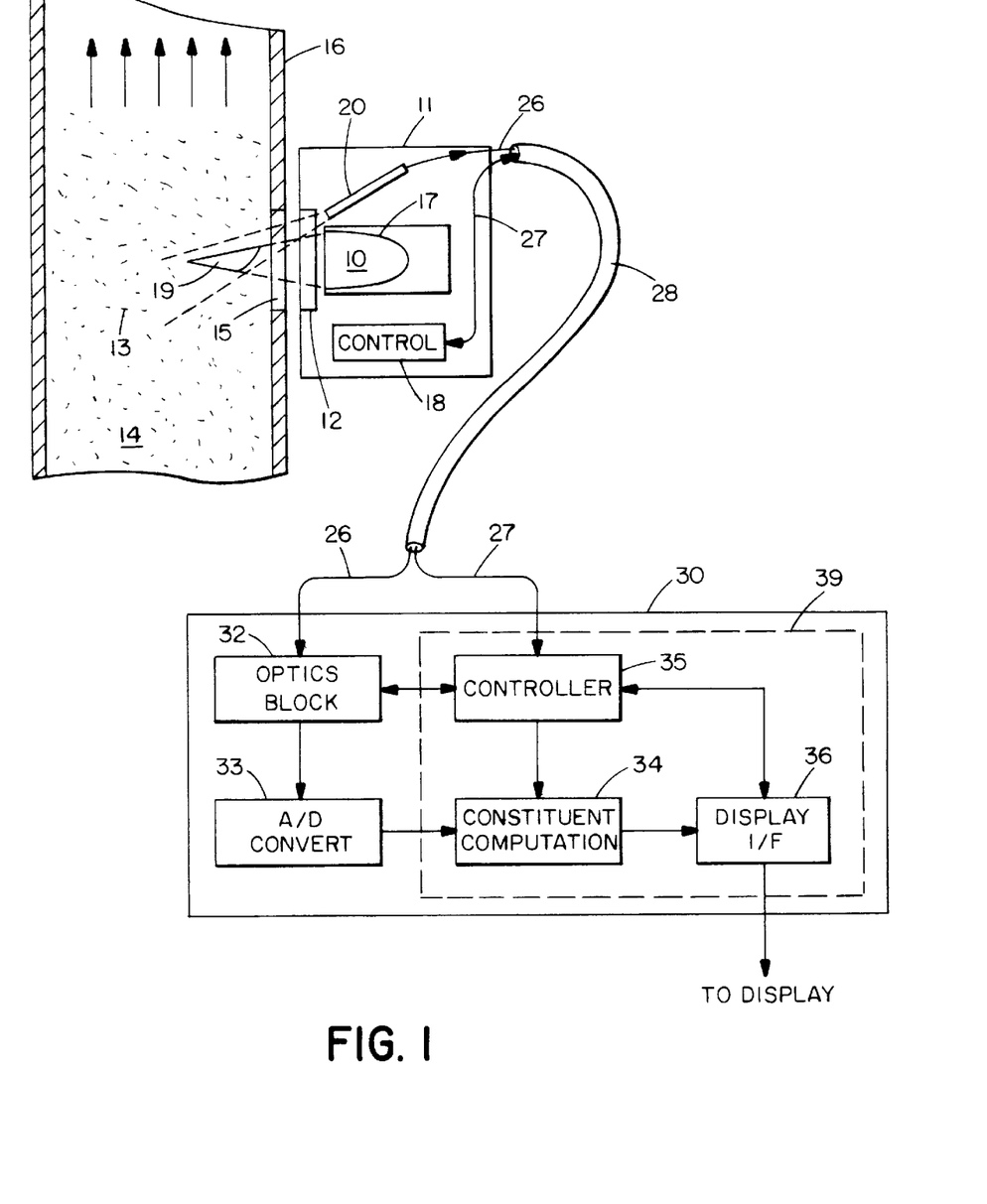
FIG. 1 is a high level schematic illustration of a short wave near infrared grain quality analysis system according to the invention.

Referring now more particularly to FIG. 1, the present invention is a system 1 for analyzing the constituent components of a flowing stream of an agricultural product as it is being processed or harvested. The agricultural products which may be analyzed by the system 1 include, but are not limited to, cereal grains such as wheat, corn, rye, oats, barley, rice, soybeans, amaranth, triticale, and other grains, grasses and forage materials. The constituent components being analyzed may include, but are not limited to, protein, oil, starch, fiber, moisture, carbohydrates and other constituents and physical characteristics such as hardness. Although the following discussion describes a particular example wherein the product being analyzed is a cereal grain, it should be understood that other agricultural products may be analyzed as well.

The system 1 uses a suitable continuous irradiating device such as an infrared light source 10. Radiation from the light source 10 shines forward through a window 12 to a sample of a flowing agricultural product 14 being harvested, processed, or otherwise flowing through a conveyance such as a duct 16.

The light source 10 continuously and simultaneously produces infrared light of multiple wavelengths in an extended short wave region of interest such as from about 570 to about 1120 nanometers (nm). The preferred light source 10 is a quartz halogen or tungsten filament bulb such as is widely available. A typical light source 10 is a tungsten filament bulb operating at 5 volts (VDC) and drawing one amp of current. The light source 10 may be further stabilized by filtering or by using an integral The light source 10 is positioned to shine upon the cereal flowing product 14 as it is flowing through a conveyance such as a duct 16 such as may be disposed within an agricultural combine or other grain processing apparatus. The flow of the agricultural product 14 through the duct 16 is generally in the direction of the illustrated arrows.

The light source 10 and related components positioned adjacent the duct 16 may be placed within a suitable sensor head housing 11. In such an instance, a window 12 is preferably disposed between the light source 10 and the flowing agricultural product 14. The window 12 is formed of a suitable material, such as sapphire, which is transparent at the wavelengths of interest, and which does not see a significant absorption shift due to temperature changes. The window 12 may be integrally formed with the housing 11 or the duct 16 as desired.

The sensor head housing 11, including the light source 10, window 12, and other related components to be described, is thus positioned to monitor a continuous flow of the agricultural product 14 through the duct 16. This may be accomplished by mounting the housing 11 such that the window 12 is disposed adjacent an opening 15 in the duct 16 so that the light source 10 shines through the window 12 and opening 15 onto the flowing product 14.

The sensor head housing 11 may be a separate physical housing or it may be integrally formed with the duct 16.

A parabolic reflector or mirror 17 is also preferably disposed within the housing 11 to collimate the output of the light source 10 into a beam 13 of approximately one centimeter in focal length. The parabolic mirror 17 focuses the light source 10 within the stream of flowing product 14.

In an alternate embodiment, more than one light source 10 can be used, such as an array of infrared emitters, as long as they are focused on the same point.

It is preferred that the light source 10 be placed such that it directly illuminates the flowing product 14 through the window 12 with no fiber optic or other device other than the window 12 itself being disposed between the light source 10 and the flowing product 14.

Control electronics 18 may also be disposed within the housing 11 to operate a shutter as will be described more fully below in connection with FIG. 2.

Light emitted by the light source 10 thus passes through the window 12 and opening 15 and is diffusely reflected from the flowing product 14. A fiber optic pickup 20, preferably also disposed within the same housing 11, is arranged to collect a portion of the diffusely reflected light from the flowing product 14. Although these diffuse reflections are primarily from the focal point of the light source 10, it should be understood that light is actually returned from a sample volume 19 defined by the intersection of the beam 13 produced by the light source 10 and the aperture or "field of view" of the fiber optic pickup 20.

The fiber optic pickup 20 is typically a communications grade optical fiber. It would typically range in diameter from about 62.5 micrometers ($\mu$m) up to about 1 millimeter (mm). One suitable fiber is 600 $\mu$m in diameter within an NA of 0.22 (f# of approximately 2.3). The pickup 20, preferably disposed at an angle with respect to the window 12 suitable to collect diffusely reflected light but not significant window surface reflection, so that light from the window 12 fills the aperture of the receiving fiber optic 20. A suitable angle may be, for example, 45°.

The output of the fiber optic pickup 20 is then fed through an optical fiber 26 to a detector and electronics block 30 to determine the constituent components of the flowing product 14. The detector and electronics block 30 includes an optics block 32, an analog to digital converter 33, a constituent computation function 34, a controller 35, and a display interface 36. The constituent computation function 34, controller 35, and display interface 36 are preferably implemented as software in a computer, microcontroller, microprocessor and/or digital signal processor 39. The functions of the electronics block will be described in further detailed below.

Figure 2A:
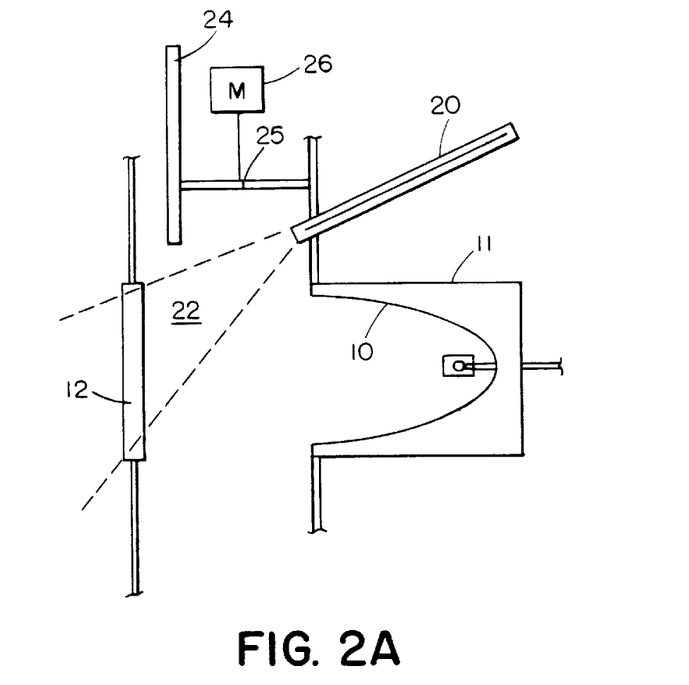
FIGS. 2A and 2B are more detailed views of a light source and detector showing their mechanical configuration with respect to a grain duct, also showing the open and closed positions of a pick up shutter.

As more particularly shown in FIG. 2A, in a preferred embodiment, the housing 11 and window 12 may be positioned such that a space 22 is formed between them for the placement of a reference flag or shutter 24. The reference shutter 24 is formed of a high diffuse reflectance material such as Spectralon™ (a pressed silicate obtained from Labsphere, North Sutton, N.H.) or a ceramic.

Figure 2B:
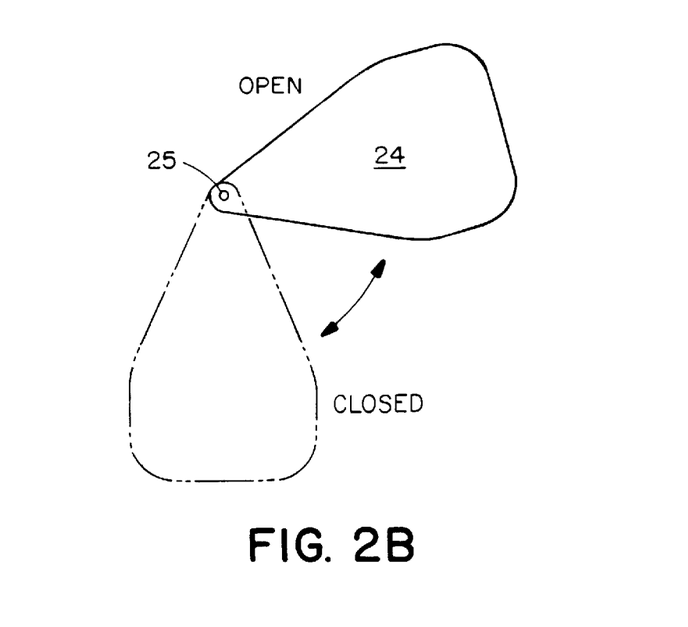

The shutter 24 is positioned so that it can be selectively moved into or out of position adjacent the end of the pick-up 20. The shutter 24 is thus typically mounted on a control device such as a motor shaft 25 driven by a motor 29 which may be activated by the controller 35 in the electronics block 30. The motor 29 permits the controller 35 to selectively choose a closed or open position for the shutter 24 as shown in the front view of FIG. 2B.

An electronic signal or signals 27 are connected between the electronics block 30 and sensor head 11 to provide a way for the controller 35 to pass signals to control the position of the shutter 24. For example, the shutter 24 is placed in the open position to allow light to pass to the sample and to be diffusely reflected by the flowing product sample 14 during sample measurement operations, and placed in a closed position to occlude light from the sample and diffusely reflected light from the shutter 24 during reference measurements, as will be described in further detail below.

The optical fiber and electronic signals 27 may be bundled together in a cable sheath 28 which is connected between the detector head housing 11 and detector and electronics block 30. In a practical deployment of the system 1 such as in an agricultural harvester, it is preferred that the cable sheath 28 be sufficiently long such that detector head housing 11 can be placed adjacent the grain chute 16 while the detector and electronics block 30 may be placed in a less harsh environment such as back in the cab of the harvester. Such a distance may be three meters, or more or less, for example.

Alternatively, the sensor head 11 and all or part of the electronics block 30 may be mounted adjacent the chute 16, in which case the optical fiber 26 will not be needed.

Although a relatively large 600 $\mu$m diameter fiber optic pick up 20 is relatively good at collecting light, it is quite probable that in practical situations, the cable 28 and thus the fiber optic 26 within it will be, at the least, required to be bent to fit in and/or around the body and other parts of the harvester. In the usual case, the cable 28 is also subjected to vibrations as the harvester travels through a field reaping the flowing product 14.

Unfortunately, vibrations associated with an operating harvester or other machinery can cause undesirable modal disturbances within the optical fiber 26. These modal disturbances are created in the form of higher order reflections such that the optics block 32 may have unwanted detection modes. These modal disturbances thus in turn cause undesirable changes in light intensity which are unrelated to the properties of the flowing product 14 and which therefore add considerable noise to the desired measurement of the properties of the flowing product 14.

In order to overcome this difficulty, the detector and electronics block 30 are implemented in a particular preferred manner. Turning attention more particularly to FIG. 3, the detector and electronics block 30 include a mode mixer 42, a fiber section 44, and a detector block 46 which itself includes a pair of cylindrical lenses 48-1, 48-2, a wavelength separator 50, and a detector 52.

Figure 3:
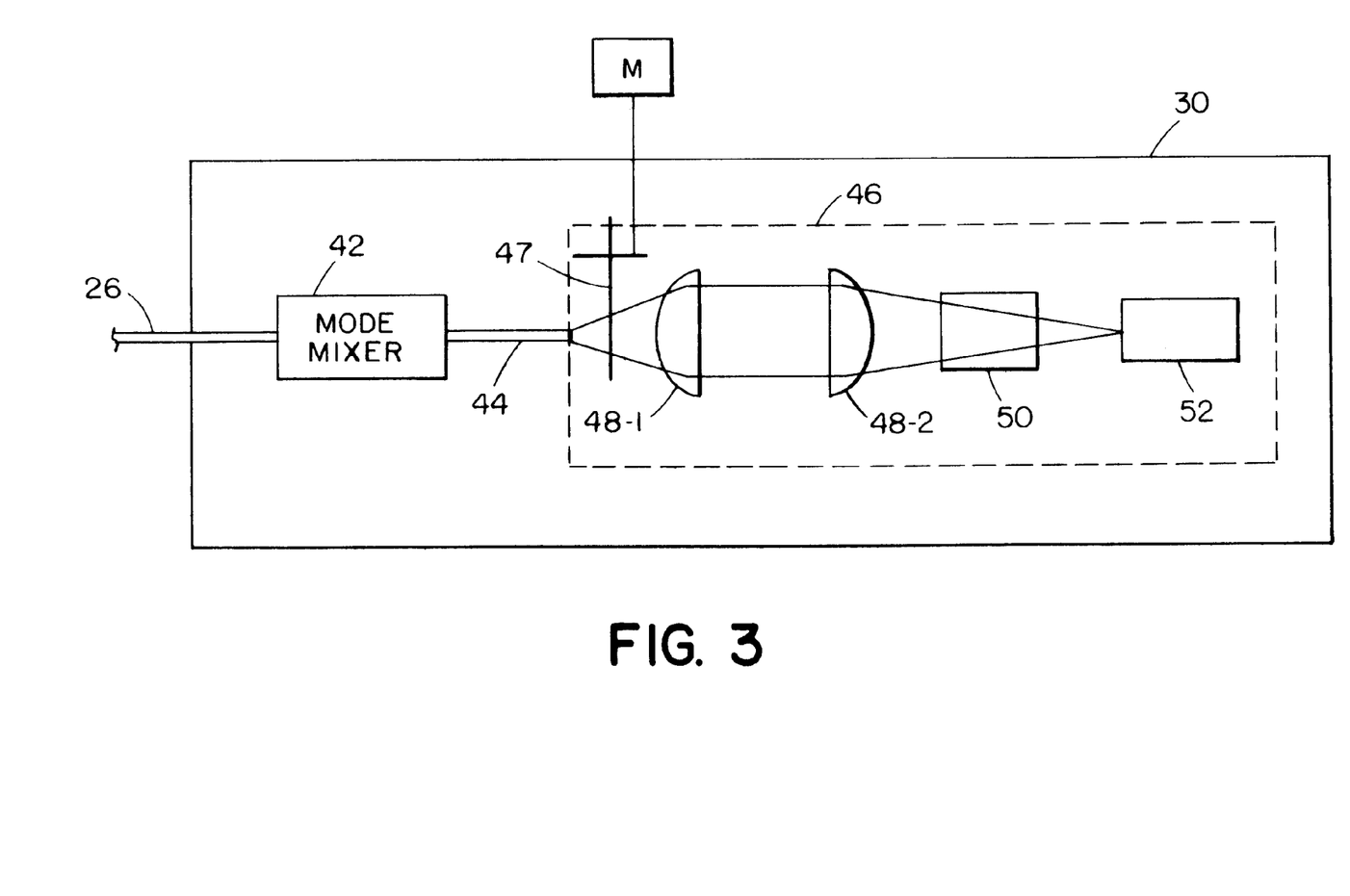
FIG. 3 is a more detailed view of an optics block showing a mode mixer, optics block shutter, filter, and optical detector components.

The mode mixer 42 is coupled to receive the light output of the optical fiber 26 and serves to remove the higher order modes from the received optical signal. The mode mixer 42 may be implemented using a number of different components.

For example, one technique for implementing the mode mixer 42 is to use one or more, preferably one, so called "grin" lenses. The grin lenses have a center wavelength of approximately the same as the center of the infrared region of interest, which here is 800 nanometers (nm). The grin lenses also have a collectively relatively high pitch of from about 0.4 to 0.5. For example, two grin lenses may be used, each having a pitch of about 0.2 to 0.25. The relatively high collective pitch provides an approximately spot-oriented image, rather than a cone type image, at the output. A suitable grin lens can be obtained from NSG Corporation of Somerset, N.J.

The mode mixer 42 may also be implemented as a holographic diffuser. In some instances a holographic diffuser may represent a more desirable implementation of the mode mixer 42 since its response is not as wavelength dependent as a grin lens. However, a grin lens is easier to manufacture on a "one-off" basis. One type of suitable holographic diffuser is the "Beam Homogenizer" available from Digital Optics Corporation of Charlotte, N. C.

The fiber coupling 44 provides a mechanically stable light pipe for coupling the output of the mode mixer 42 to the rest of the optics block 46.

Another shutter 47 is preferably disposed at the output of the fiber coupling. This optical block shutter 47 is formed of an opaque material and is used to block light from entering the optics block 46 during collection of a reference dark spectrum procedure which is described in greater detail below.

The cylindrical lenses 48-1 and 48-2 serve to properly focus the received light energy at the input of the optics block 46 onto the detector 52.

The wavelength separator 50 provides spatial separation of the various wavelengths of diffusely reflected light energy of interest. Suitable wavelength separators 50 include linearly variable filters (LVF), gratings, prisms, interferometers or similar devices. The wavelength separator 50 is preferably implemented as a linearly variable filter (LVF) having a resolution ($\Delta\lambda/\lambda$) of approximately one to four percent.

The now spatially separated wavelengths in turn focus upon the detector 52. The detector 52 is such that it simultaneously measures the response at a broad range of wavelengths. In the preferred embodiment, the detector 52 is an array of charge coupled devices (CCDs), which individually measure the light intensity at each of the respective wavelengths. In other words, each cell of the CCD array is tuned to measure the intensity of an individual bandpass of light.

Other suitable detectors 52 may, however, be constructed from fast scan photodiodes, charge injection devices (CIDs), or any other arrays of detectors suitable for the task of simultaneously detecting, in parallel, the wavelengths of interest.

In a preferred embodiment, the detector 52 is a silicon CCD array product, such as a Fairchild CCD 133A available from Loral-Fairchild. The device preferably has a spatial resolution of about 13 micrometers. The frequency resolution is the selected bandwidth of interest (as determined by the linear variable filter 50), divided by the number of CCD elements. In the preferred embodiment the CCD array 52 is a 1,024 element array processing wavelengths in the range from about 570 to about 1120 nm.

In addition, the detector 52 such as a CCD array is typically temperature sensitive so that stabilization is usually preferred.

In the preferred embodiment, because of the compact design of the optics module 46 and the relatively close positioning of LVF 50 and CCD array 52, both of these components can be temperature stabilized together. The temperature stabilization can be by suitable heat sink surfaces, a thermoelectric cooler (Peltier cooler) or fan.

Returning attention to FIG. 1, the individual electrical signals provided by the CCD for each wavelength are then fed from the output of the detector 52 to be converted to digital signals by the analog to digital converter 33.

A computation block 34, preferably implemented in a microcomputer or digital signal processor as described above, then carries out calculations on the basis of the received wavelength intensities to obtain percentage concentrations of constituents of the sample 14. The percentage of constituents, which are determined using a chemometric model, are then shown in any desired way such as by a meter or presenting them to a display. The display may be integral to a laptop computer or other computer placed in the cab of the harvester. The computation block may be part of the electronics block 30 or may physically separate from it.

Techniques for calculating percentage concentrations of grain based upon samples of light and particular wavelengths are the multi-variate techniques detailed in the book by Sharaf, M. A., Illman, D. L., and Kowalski, B. R., entitled "Chemometrics" (New York: J. Wiley & Sons, 1986).

Preferred wavelengths of interest depend upon the constituents being measured. For example, when measuring protein concentration, the algorithms make use of absorptance attributable to the vibration-rotational overtone bands of the sub-structure of protein. At longer wavelengths absorptivity coefficients are large, the path length is short, and thus one would not sample the interior of the grain particles. At shorter wavelengths the absorptivity coefficients are small and the signal is thus weak.

The system 1 thus provides for irradiation of the sample followed by spacial separation and detection of multiple wavelengths in parallel, making for rapid analysis of this sample. Moreover, because the optical portions of the unit are stabile to vibrations, it is substantially insensitive to vibrations such as found in agricultural combines or other harvesting and processing equipment. The system 1 may therefore be easily deployed in environments where real time analysis of harvested grain or other agricultural produce may be carried out during harvesting and other processing operations. The data obtained thereby may be compared with reference data to provide percentage concentrations of constituents for use in mapping field layout according to the so called global positioning system (GPS).

Furthermore, the use of the CCD array 52 provides advantages over prior art techniques that use discrete or scanned diode arrays. In particular, the CCD bins are all filed with charge at the same time in parallel with one another, until one of them is nearly full. They are then emptied and the results read out by the controller 35 while the CCD array begins filling again. Therefore, each pixel has seen the same grains over the same time intervals. In contrast, diode arrays must be read sequentially so that for example, any given element is producing a signal from a volume of grain if it is distinct from those seen by previous pixels.

The signal to noise ratio of the system 1 may be improved by averaging over the course of many measurements.

Briefly mentioned above was a procedure for calculating an absorption spectrum. To this end, the step motor 26 (FIG. 2A) can be activated to place the shutter 24 in the closed position between the end of the pick up 20 and the optics block 46. In this position, the optics block 46 therefore sees no light from the pick up 20 and only the white light emissions of the shutter blade 24. This measurement then permits a reference signal to be measured.

Figure 4:
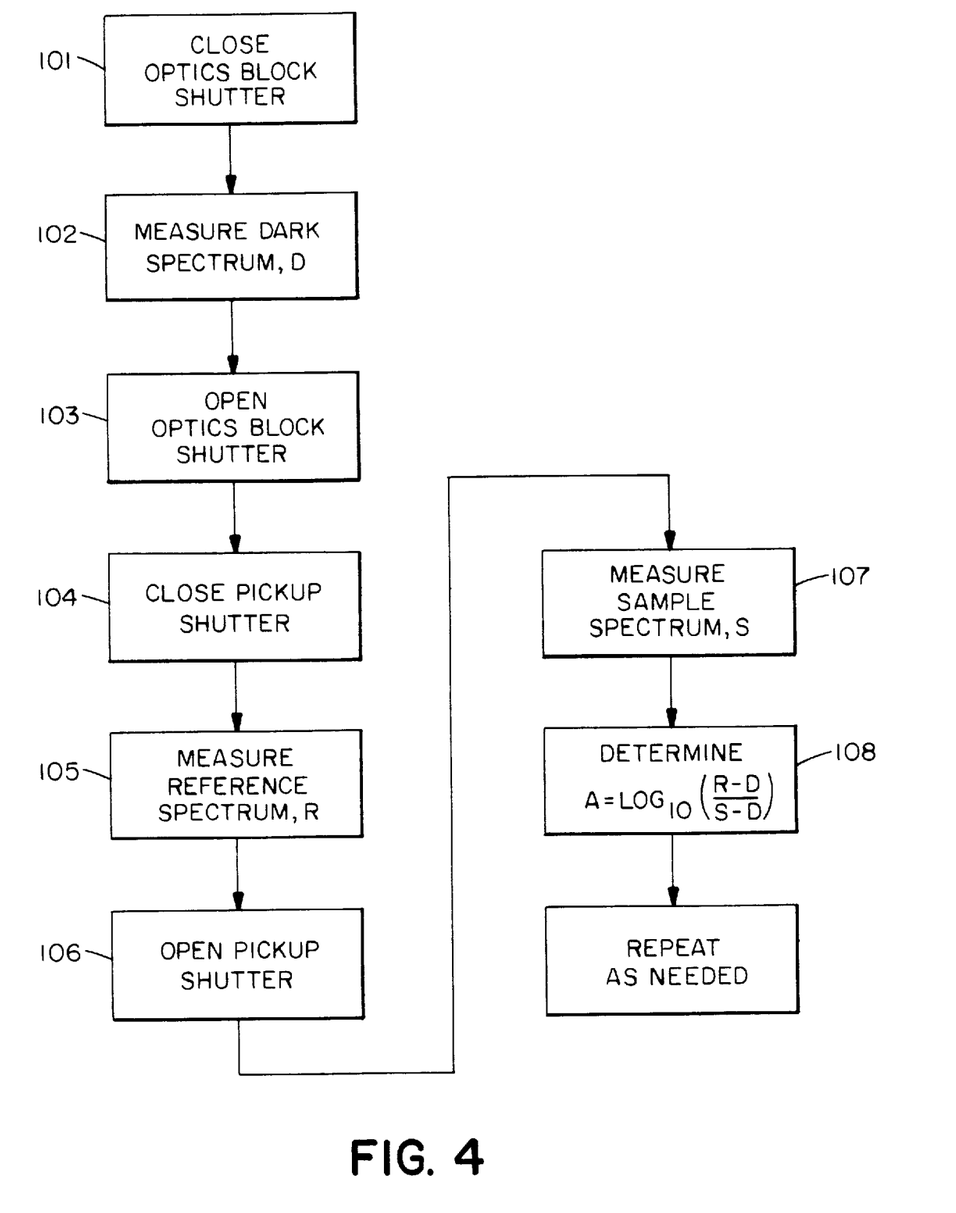
FIG. 4 depicts a process for the system for measuring aborptivity.

The preferred absorptivity measurement includes the following process (also depicted in FIG. 4):

1. A reference dark spectrum, D, is measured by closing the optics block shutter 47 (step 101).
2. A reading is then taken from the CCD array 52 (step 102).
3. Open the optics block shutter 47 (step 103).
4. Close the pick up shutter 24 (step 104).
5. Measure a reference spectrum, R, by taking a reading from the CCD array 52 (step 105).
6. Open the pick up shutter 24 (step 106).
7. With both shutters 24 and 47 now open, take a reading from the sampled volume 19 to determine a sample spectrum, S (step 107).
8. Calculate the absorptance spectrum, A (step 108).

The light absorption as derived from these diffuse reflectance measurements is given by $$A = \text{LOG}_{10}(R-D/S-D).$$

In addition, since the absorptivity variations from the presence of protein are quite small, multiple realizations (step 109), averaging, and second derivative analysis are typically used to produce the desired absorptivity number at a particular wavelength Further data processing therefore may provide a second derivative of this function to remove constant and linear offsets so that only quadratic and higher order features in the absorptivity spectrum are utilized in the determination of protein content.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. An apparatus for determining a constituent component of a flowing stream of an agricultural product as it is being harvested on a real time basis, the apparatus being attached to mobile agricultural equipment, the apparatus comprising:

a light source, arranged to irradiate a sample portion of the flowing stream of agricultural product as it is being processed with a plurality of wavelengths within a selected irradiation bandwidth within a near infrared spectrum;

an optical pick up, arranged to receive light energy reflected from the irradiated sample portion;

a wavelength separator, connected to receive light from the optical pick up, and to produce spatially separated light of different wavelengths; and a detector, connected to receive light from the wavelength separator, and to produce detected intensity signals indicative of light intensity within the wavelength separator bandwidth.

2. An apparatus as in claim 1 wherein the wavelength separator and detector are arranged such that the detected intensity signals at a given sample time represent the response of the apparatus for a range of wavelengths as taken from a sample portion of the flowing stream.

3. An apparatus as in claim 1 wherein the wavelength separator is a linearly variable filter.

4. An apparatus as in claim 1 wherein the flowing stream of agriculture product is located in an agriculture combine.

5. An apparatus as in claim 1 wherein the detector further comprises a detector array connected to produce detected intensity signals indicative of light intensity simultaneously at multiple selected wavelengths.

6. An apparatus as in claim 1 wherein the constituent component is selected from the group consisting of protein, moisture, oil, starch, flour, and hardness.

7. An apparatus as in claim 1 additionally comprising:
an optical fiber, disposed between the optical pick up and the wavelength separator, to couple light energy from an input end to an output end thereof.

8. An apparatus as in claim 7 additionally comprising:
a mode mixer, disposed at the output end of the optical fiber, to attenuate variations in optical intensity of the light from the pick up introduced by the optical fiber.

9. An apparatus as in claim 1 additionally comprising:
an analog to digital converter, connected to receive the detected intensity signals and to provide detected intensity values.

10. An apparatus as in claim 9 additionally comprising:
a computer, connected to receive the detected intensity signals from the detector, and to calculate constituent components of the sample portion of the agricultural product from the detected intensity values.

11. An apparatus as in claim 10 wherein the computer repeats the calculation steps above and averages measurements of a reference spectrum, R, and a sample spectrum, S, to determine the absorption value.

12. An apparatus as in claim 1 wherein the light source and optical pick up are placed in an optical head housing positioned adjacent a side opening in a product chute, and the wavelength separator and detector are placed remotely from the product chute, and wherein an optical fiber is connected between the optical pick up and the wavelength separator to couple light energy between them.

13. An apparatus as in claim 1 wherein the detector is a charge coupled device (CCD) array.

14. In a harvester which includes a product chute for conveying a flowing stream of agricultural product, an analyzer for determining constituent components of the agricultural product as it is being harvested, the analyzer comprising:
a light source, arranged to irradiate a sample portion of the flowing stream of agricultural product as it is fed through the chute, the light source providing a plurality of wavelengths within a selected optical irradiation bandwidth;
an optical pick up, for receiving light energy reflected from the irradiated sample portion;
a wavelength separator, receiving light from the optical pick up, and producing spatially separated light of different wavelengths;
a detector, receiving light from the wavelength separator, and producing detected intensity signals indicative of light intensity simultaneously at multiple selected wavelengths within the dispersing filter bandwidth; and
a computer, for receiving the detected intensity signals from the detector, and for calculating constituent components of the sample portion of the agricultural product from the detected intensity values.

15. A short wavelength-near infrared analysis system for obtaining percentage concentrations of constituents of a composite substance, comprising:
means for irradiating a composite substance simultaneously with short wavelength—near infrared radiation over a specified bandwidth;
means for picking-up electromagnetic radiation reflected from said composite substance;
means for mode mixing the reflected electromagnetic radiation to attenuate variations in intensity due to vibration;
means for spatially separating wavelengths of the reflected electromagnetic radiation as produced by the means for mode mixing;
means for individually detecting in parallel the wavelengths of the spatially separated electromagnetic radiation to obtain percentage concentration of the various constituents of said component substance; and
wherein the analysis system is attached to an agricultural combine for analyzing a flowing stream of agricultural produce on a real time basis during harvesting thereof.

16. A method for determining a constituent component of a flowing stream of an agricultural product as it is being harvested on a real time basis within mobile agricultural equipment, the method comprising the steps of:
irradiating a sample portion of the flowing stream of agricultural product as it is being processed with a plurality of wavelengths within a selected irradiation bandwidth within a near infrared spectrum;
picking up light energy reflected from the irradiated sample portion;
separating wavelengths of the picked up reflected light to produce spatially separated light of different wavelengths; and
detecting intensity signals from the separated wavelengths at multiple selected wavelengths to determine multiple light intensities.

17. A method as in claim 16 wherein the steps of separating and detecting are performed such that the detected intensity signals at a given sample time represent the response for a range of wavelengths as taken from a single sample portion.

18. A method as in claim 16 wherein the step of separating is performed by a linearly variable filter.

19. A method as in claim 16 wherein the flowing stream of agriculture product is located in an agricultural combine.

20. A method as in claim 16 additionally comprising the steps of:
mode mixing the light energy provided by the picking up step, to attenuate variations in optical intensity of the light.

21. A method as in claim 16 additionally comprising the step of:
converting the detected intensity signals to provide digital detected intensity values.

22. A method as in claim 16 additionally comprising the step of:
calculating constituent components of the sample portion of the agricultural product from the detected intensity values.

23. A method as in claim 22 additionally comprising the steps of:
selectively performing the step of picking up diffusely reflected light by operating a pick up shutter in a closed or open position;
selectively performing the step of separating wavelengths by operating an optics block shutter, in a closed or open position; and
wherein the step of calculating constituent components by determining an absorptivity by the steps of:
measuring a dark spectrum, D, as the response with the optics block shutter closed;
measuring a reference spectrum, R, by opening the optics block shutter and closing the pick up shutter;

measuring a sample spectrum, S, with both shutters open; and determining a light absorption value, A, at the selected wavelength from the relationship $$A = \mathrm{LOG}_{10}(R-D/S-D).$$

24. A method as in claim 23 wherein the step of calibrating is repeated to average measurements of a reference spectrum, R, and a sample spectrum, S, to determine the absorption value.

25. An apparatus for determining at least one constituent component of a flowing stream of an agricultural product as it is being harvested on a real time basis, the apparatus comprising:

a light source, arranged to irradiate a sample portion of the flowing stream of agricultural product as it is being harvested with a plurality of wavelengths within a selected irradiation bandwidth within a near infrared spectrum;

an optical pick up, arranged to receive light energy reflected from the irradiated sample portion;

a linear variable filter, connected to receive light from the optical pick up, and to produce spatially separated light of different wavelengths;

an optical fiber, disposed between the optical pick up and the wavelength separator, to couple light energy from the optical pick up to the linear variable filter; and a charge coupled device detector array connected to receive light from the wavelength separator, and to produce detected intensity signals indicative of light intensity at multiple selected wavelengths within the dispersing filter bandwidth.

26. An apparatus as in claim 25 wherein the wavelength separator and detector are arranged such that the detected intensity signals at a given sample time represent the response of the apparatus for a range of wavelengths as taken from a sample portion of the flowing stream.

27. An apparatus as in claim 25 additionally comprising:

a mode mixer, coupled to the optical fiber, to attenuate variations in optical intensity of the light from the pick up introduced by the optical fiber.

28. An apparatus as in claim 25 wherein the flowing stream of agricultural product is in an agricultural combine.

29. An apparatus as in claim 25 wherein the flowing stream of agricultural product is in a grain processor.

30. An apparatus as in claim 25 wherein the flowing stream of agricultural product is in a storage facility.

31. An apparatus as in claim 25 wherein the constituent component is selected from the group consisting of protein, moisture, oil, starch, density, and hardness.

32. An apparatus as in claim 25 wherein the light source and optical pick up are placed in an optical head housing positioned adjacent an opening in a product chute, and the wavelength separator and detector are placed remotely from the product chute, and wherein an optical fiber is connected between the optical pick up and the wavelength separator to couple light energy between them.

33. An apparatus as in claim 25 additionally comprising:

an analog to digital converter, connected to receive the detected intensity signals and to provide detected intensity values.

34. An apparatus as in claim 33 additionally comprising:

a computer, connected to receive the detected intensity signals from the detector, and to determine the percentage of at least one constituent component present in the sample portion of the agricultural product from the detected intensity values.

35. An apparatus as in claim 34 wherein the computer repeats the determination steps above to determine an average value for the percentage of at least one constituent component.

36. A short wavelength-near infrared (SW-NIR) analysis system for obtaining percentage concentrations of constituents of a composite substance, comprising:

means for irradiating a composite substance simultaneously with short wavelength-near infrared (SW-NIR) radiation;

means for simultaneously picking-up electromagnetic radiation reflected from different parts of said composite substance;

means for spatially separating a plurality of wavelengths of the reflected electromagnetic radiation;

means for individually detecting in parallel a plurality of wavelengths of the reflected electromagnetic radiation to obtain percentage concentration of the various constituents of said composite substance; and wherein the SW-NIR analysis system is attached to an agricultural combine for analyzing a flowing stream of agricultural produce on a real time basis during harvesting thereof.

37. A method for determining at least one constituent component of a flowing stream of an agricultural product as it is being harvested on a real time basis, the method comprising the steps of:

irradiating a sample portion of the flowing stream of agricultural product while it is being harvested with a plurality of wavelengths within a selected irradiation bandwidth within a near infrared spectrum;

picking up light energy reflected from the irradiated sample portion;

separating wavelengths of the picked up reflected light to produce spatially separated light of different wavelengths; and detecting intensity signals from the separated wavelengths simultaneously at multiple selected wavelengths to simultaneously determine light intensity at multiple wavelengths.

38. A method as in claim 37 additionally comprising the step of:

mixing the light energy provided by the picking up step to attenuate variations in optical intensity of the light.

39. A method as in claim 37 wherein the steps of separating and detecting are performed such that the detected intensity signals at a given sample time represent the response for a range of wavelengths as taken from a sample portion.

40. A method as in claim 37 wherein the step of separating is performed by a linearly variable filter.

41. A method as in claim 37 wherein the flowing stream of agricultural product is in an agricultural combine.

42. A method as in claim 37 wherein the flowing stream of agricultural product is in a grain processor.

43. A method as in claim 37 wherein the flowing stream of agricultural product is in a storage facility.

44. A method as in claim 37 additionally comprising the step of:

converting the detected intensity signals to provide digital detected intensity values.

45. A method as in claim 37 additionally comprising the step of:

determining at least one constituent component of the sample portion of the agricultural product from the detected intensity values.

46. A method as in claim 45 additionally comprising the steps of:

selectively performing the step of picking up reflected light by operating a pick up shutter in a closed or open position;

selectively performing the step of separating wavelengths by operating an optics block shutter, in a closed or open position; and wherein the step of determining at least one constituent component by determining an absorptivity further comprises the steps of:

measuring a dark spectrum, D, as the response with the optics block shutter closed;

measuring a reference spectrum, R, by opening the optics block shutter and closing the pick up shutter;

measuring a sample spectrum, S, with both shutters open; and determining a light absorption value, A, at the selected wavelength from the relationship $$A = \text{LOG}_{10}(R-D/S-D).$$

47. A method as in claim 46 wherein the step of calculating is repeated to average measurements of R and S to determine the absorption value.

* * * * *

US006100526C1

(12) EX PARTE REEXAMINATION CERTIFICATE (10132nd)
United States Patent
Mayes (10) Number: US 6,100,526 C1
(45) Certificate Issued: Apr. 25, 2014

(54) GRAIN QUALITY MONITOR (75) Inventor: David M. Mayes, LaGrande, OR (US)

(73) Assignee: Textron Systems Corporation, Wilmington, MA (US)

Reexamination Request:
No. 90/020,024, Sep. 14, 2012

Reexamination Certificate for:
Patent No.: 6,100,526
Issued: Aug. 8, 2000
Appl. No.: 09/019,667
Filed: Feb. 6, 1998

Related U.S. Application Data (63) Continuation-in-part of application No. 08/777,228, filed on Dec. 30, 1996, now abandoned.

(51) Int. Cl.
G01N 21/31 (2006.01)
G01N 21/35 (2014.01)
A01D 41/127 (2006.01)
G01N 21/47 (2006.01)
G01N 21/85 (2006.01)

(52) U.S. Cl.
CPC ............ A01D 41/127 (2013.01); G01N 21/359 (2013.01); G01N 21/474 (2013.01); A01D 41/1277 (2013.01); G01N 21/3563 (2013.01); G01N 21/85 (2013.01); G01N 2021/8592 (2013.01)
USPC .................................................... 250/339.11

(58) Field of Classification Search
None
See application file for complete search history.

(56) References Cited

To view the complete listing of prior art documents cited during the proceeding for Reexamination Control Number 90/020,024, please refer to the USPTO's public Patent Application Information Retrieval (PAIR) system under the Display References tab.

Primary Examiner — Albert J Gagliardi (57) ABSTRACT

Percentage concentrations of constituents of a sample of cereal grain or other agricultural product in a flowing stream are determined while harvesting or processing using a short wave near infrared analyzer. The analyzer irradiates the sample, picks up diffuse reflectance of individual wavelengths from the sample and spatially separates the diffuse reflectance into a response at individual wavelengths. The result is to simultaneously detect the intensities of the individual wavelengths in parallel from the same portion of the product being analyzed. Percentage constituents of the composite substance may then be compared with known percentage constituents to determine the constituents. The analyzer is optically stabilized and is therefore suitable for attaching to the agricultural combine to perform real time measurements in the field.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-47 are cancelled.

\* \* \* \* \*